(12) United States Patent
Lai

(10) Patent No.: US 6,367,931 B2
(45) Date of Patent: Apr. 9, 2002

(54) OPTICAL TRACKING BASED ON A CHANGE IN OPTICAL REFLECTION ACROSS A REFERENCE MARK ON AN OBJECT TO BE TRACKED

(76) Inventor: Ming Lai, 5615 Cedar Crest Terrace, Dublin, CA (US) 94568

( * ) Notice: Subject to any disclaimer, the term of this patent is extended or adjusted under 35 U.S.C. 154(b) by 0 days.

(21) Appl. No.: 09/741,407

(22) Filed: Dec. 19, 2000

Related U.S. Application Data

(63) Continuation of application No. 09/300,194, filed on Apr. 27, 1999, now Pat. No. 6,179,422.
(60) Provisional application No. 60/083,248, filed on Apr. 27, 1998.

(51) Int. Cl.[7] .................................................. A61B 3/14
(52) U.S. Cl. ...................................................... 351/209
(58) Field of Search ................................. 351/206, 208, 351/209, 210, 221; 250/235; 356/445, 446, 447, 139.08; 359/385; 369/44.26

(56) References Cited

U.S. PATENT DOCUMENTS

| | | | |
|---|---|---|---|
| 4,650,325 A | * | 3/1987 | Crowder ................ 356/139.08 |
| 4,685,096 A | * | 8/1987 | Romeas ................... 369/44.26 |
| 4,764,005 A | | 8/1988 | Webb et al. |
| 4,856,891 A | | 8/1989 | Pflibsen et al. |
| 5,028,802 A | | 7/1991 | Webb et al. ................ 250/235 |
| 5,098,426 A | | 3/1992 | Sklar et al. |
| 5,345,281 A | | 9/1994 | Taboada et al. |
| 5,360,424 A | | 11/1994 | Klopotek |
| 5,410,376 A | | 4/1995 | Cornsweet et al. |
| 5,430,505 A | | 7/1995 | Katz |
| 5,620,436 A | | 4/1997 | Lang et al. |
| 5,632,742 A | | 5/1997 | Frey et al. |
| 5,645,550 A | | 7/1997 | Hohla |
| 5,752,950 A | | 5/1998 | Fret et al. |
| 5,782,822 A | | 7/1998 | Telfair et al. |
| 5,923,399 A | | 7/1999 | Van De Velde ............. 351/221 |
| 5,966,197 A | | 10/1999 | Yee ............................ 351/210 |

* cited by examiner

Primary Examiner—George Manuel
(74) Attorney, Agent, or Firm—Fish & Richardson PC

(57) ABSTRACT

An optical tracking device and method are disclosed for tracking lateral movement of an object. A scanning probe beam and a time-resolved detection are implement in the disclosed technique. A particular application is for tracking the eye movement during a laser surgery.

20 Claims, 8 Drawing Sheets

OPTICAL TRACKING BASED ON A CHANGE IN OPTICAL REFLECTION ACROSS A REFERENCE MARK ON AN OBJECT TO BE TRACKED

This application is a continuation of the U.S. application Ser. No. 09/300,194, is now U.S. Pat. No. 6,179,422, filed on Apr. 27, 1999, which claims the priority from the U.S. Provisional Application No. 60/083,248, filed on Apr. 27, 1998.

TECHNICAL FIELD

The present invention relates to tracking an object by optical means, and more specifically, to automatic monitoring and tracking a movable object such as an eye.

BACKGROUND

Monitoring and tracking a laterally movable object are important in many applications. In certain applications, it is desirable to have a tracking device not only to monitor the displacement of the object but also to follow the movement of the object without a significant delay. Tracking and following the eye movement during a laser eye surgery is an example of such applications.

Many eye-tracking devices have been developed for eye surgery with lasers, in particular, for photo-refractive surgery. A typical photo-refractive surgery scans an UV laser beam on the cornea to sculpture the profile of the corneal outer surface, one layer at a time. This procedure can correct various refractive disorders of the eye, including nearsightedness, farsightedness, and astigmatism.

Any eye movement during the surgery may adversely affect the outcome of refractive correction. Immobilizing the eye movement during a surgery has been proven difficult in practice. A device automatically tracking and compensating the eye movement is an attractive approach. For the nature of photo-refractive surgery, the tracking device needs to be fast, accurate, and reliable.

U.S. Pat. No. 5,620,436 discloses use of a video camera to monitor the eye's movement and to determine the position of an aiming beam on the eye. U.S. Pat. No. 5,632,742 teaches projecting four laser spots on the eye and using a set of peak-and-hold circuits to determine the position of the eye. In these designs, a ring shape reference is used for determining the eye position, and spatial stationary infrared beams are applied to illuminate the reference. Sophisticated imaging system and electronics, such as a CCD camera or four peak-and-hold circuits are implemented to determine the position of the reference. The ring shape references are practically either the limbus or the iris of the eye and the whole ring is needed as the reference for determining the eye position.

SUMMARY

Generally, any optically identifiable reference mark or indicator affix to an object can be used to indicate the position and movement of the object. The devices and methods disclosed herein apply an optical probe beam scanning repeatedly and rapidly over such a reference mark. A change in the position of the reference mark can then be determined by measuring the change in the delay between a predetermined reference time and the detected time at which the optical probe beam intercepts the reference mark. The reference mark can be artificially formed on the object, or alternatively, can be an inherent mark on the object.

For the application of eye tracking, a reference mark may be the limbus of the eye, which is the natural boundary between the transparent cornea and the white sclera. Optical scattering changes from one side of the limbus to the other significantly. Therefore the position of the limbus can be detected by measuring the timing of the change in the scattered light of the probe beam as the probe beam scans across the limbus. The devices and methods of the present disclosure will be described by examples of eye tracking using a section of the limbus as the reference mark.

In one embodiment, a section of the limbus is used as the reference mark and the x-y positions of the limbus are determined by two sets of linear positioning devices. The two linear positioning devices are set for measurement along two mutually orthogonal axes.

Each linear positioning device includes a scanning beam generator, a detection assembly, and a processing electronics. The scanning-beam generator projects an infrared probe beam onto the eye and scans the probe beam across a section of the limbus repetitively. The detection assembly detects the infrared light scattered from the eye. The detected scattered-light signal is a time-resolved signal and has a sequence of sharp steps corresponding to the probe beam repeatedly across the limbus. The timing of each sharp step depends on the limbus position at the corresponding scan. The processing electronics converts the timing of the sharp steps into the positioning signal indicating the position of the eye.

With the positioning signal, a system computer can then generate a control signal to steer the surgical laser beam to follow the movement of the eye. Hence, accurate laser surgery can be achieved even though the eye may move during the surgery.

In this embodiment, about a quart of the limbus is used to determine the x and y positions of the eye. This is particularly important for a new type of refractive surgery so called LASIK, in which part of the limbus is obstructed during the surgery. This embodiment can use the limbus section that is not blocked and thus it can use the limbus as a reliable reference mark for LASIK.

DETAILED DESCRIPTION

Figures 1, 1A:
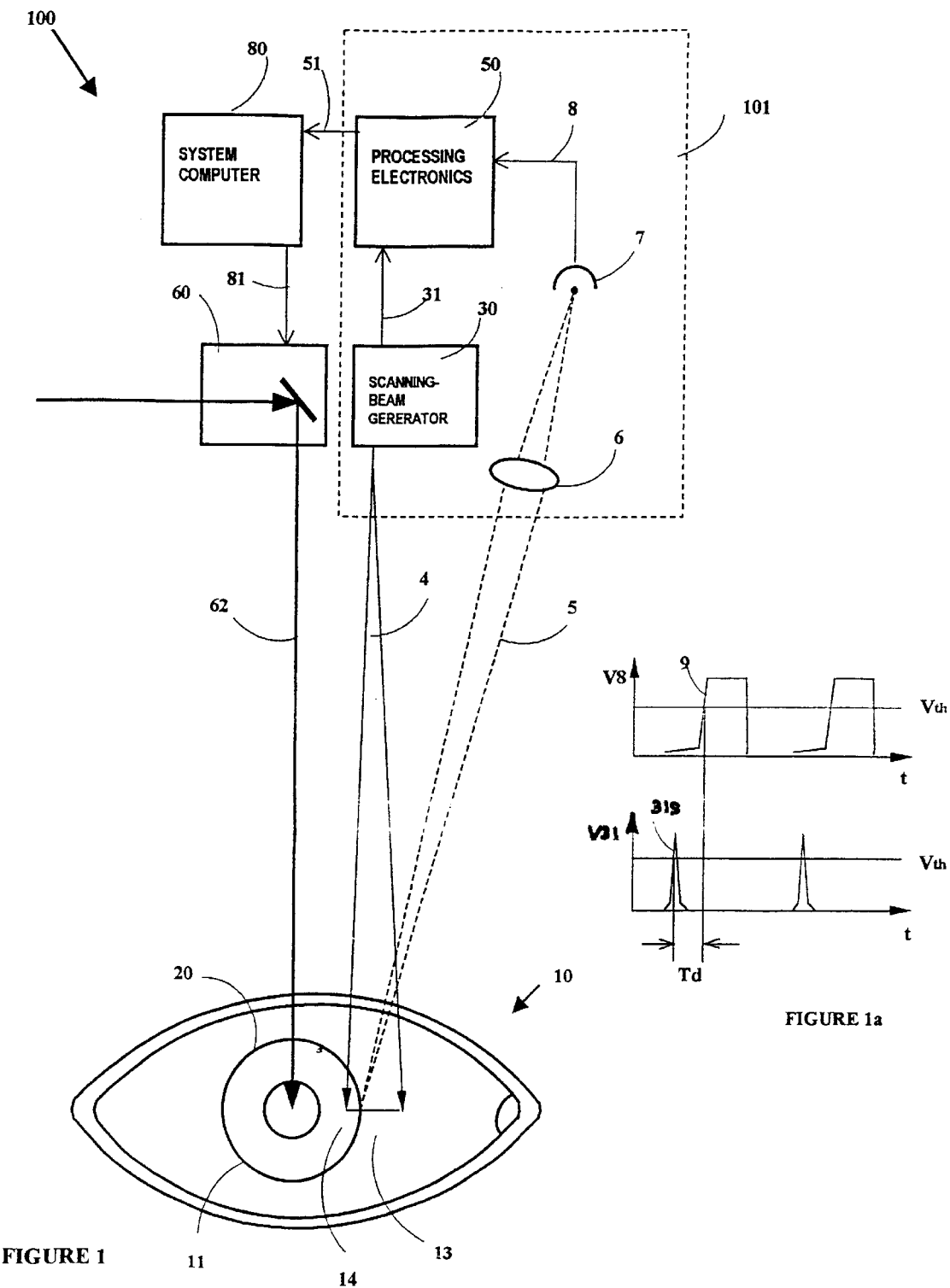
FIG. 1 is a schematic diagram showing one embodiment of an open-loop optical monitoring and tracking system.
FIG. 1a shows timing diagrams of the scattered-light signal from the eye and the reference signal generated by a scanning beam generator.

FIG. 1 shows a schematic diagram of one embodiment of an optical monitoring and tracking system 100 for an eye 10.

The system 100 implements an open loop configuration that includes a position sensing module 101, a system computer 80, and a beam steering module 60 (e.g., a x-y scanner). The position-sensing module 101 projects a scanning probe beam 4 and monitors the position of the eye 10. The system computer 80 controls the beam steering module 60 to guide a surgical laser beam 62 to a desired position on the eye 10. As an open loop configuration, the scanning probe beam 4 dose not follow the movement of the eye 10 and only one beam steering module 60 is needed.

For illustration purpose, the position-sensing module 101 shown in FIG. 1 is only a linear positioning device and is for monitoring one-dimensional eye movement only (e.g., along x-direction). To determine the eye's movement in two dimensions, a second set of linear positioning device is needed to monitor the movement of the eye 10 along a second different direction, e.g., the y-direction orthogonal to the x-direction.

The position-sensing module 101 comprises a scanning beam generator 30, a collection lens 6, a photo-detector 7, and a processing electronics 50. The limbus 11 of the eye 10 is used as a reference mark 20. The scanning-beam generator 30 projects the scanning probe beam 4 across the reference mark 20. The scanning probe beam 4 may repeatedly start from a fixed point and is scanned at a constant speed over a predetermined tracking range. The scanning-beam generator 30 also produces a reference signal 31 to indicate a reference point of the scanning.

The lens 6 is disposed at a proper position relative to the eye 10 to collect the scattered light 5. The photo-detector 7 receives and converts the scattered light 5 into an electrical signal, i.e., the scattered-light signal 8. The scattering from the sciera side 13 of the eye 10 is approximately 20 times stronger than that from the transparent cornea side 14. Hence, the intensity of the scattered light 5 exhibits a significant change when the probe beam 4 scans across the limbus 11. This intensity change of the scattered light 5, in turn, generates a sharp step in the scattered-light signal 8. The timing of this sharp step depends on the position of the eye 10.

In one implementation, an infrared laser beam (at 830 nm) of about 100 $\mu$W is used as the scanning probe beam 4 and the collection lens 6 having an aperture of about 18 mm is located about 30 cm away from the eye 10. Detector 7 receives a scattered-ligtht power of about 20 nW when the probe beam 4 is on the sclera side.

FIG. 1*a* shows timing diagrams of the scattered-light signal 8 and the reference signal 31. The scattered-light signal 8 has a sequence of sharp steps and each sharp step 9 corresponds to a scan of the probe beam 4 across the limbus 11. The sharp step 9 has a time delay Td with respect to the reference point 31s of the scanning. This time delay Td depends on the position of the limbus 11 and varies as the eye 10 moves. The processing electronics 50, which may include a microprocessor, processes the reference signal 31 and the scattered-light signal 8 to determine this time delay Td for each scan. This time delay Td is then used to determine the position of the limbus 11. The lines Vth represent the threshold voltage for triggering.

To operate the tracking device 100, an initial time delay $Td_0$ or eye position is first registered and stored in the system computer 80. The time delay Td of subsequent scans is then compared with the initial time delay $Td_0$ to calculate a displacement of the eye 10. With this calculated displacement, the system computer 80 can generate a control signal 81 to drive the beam steering module 60 to steer the surgical laser beam 62 to follow the movement of the eye 10.

As an open loop device, the scanning probe beam 4 does not move with the eye 10. The beam steering module 60 can be used simultaneously to compensate the eye movement and to scan the surgical laser beam 62 on the eye 10. In this case, the control signal 81 may include of a scanning signal and an offset signal. The scanning signal scans the surgical laser beam 62 in a predetermined pattern while the offset signal offsets the scanning to compensate for the eye movement. This open-loop device is relatively simple and can be used to accurately track small movement of the eye 10.

Figure 2:
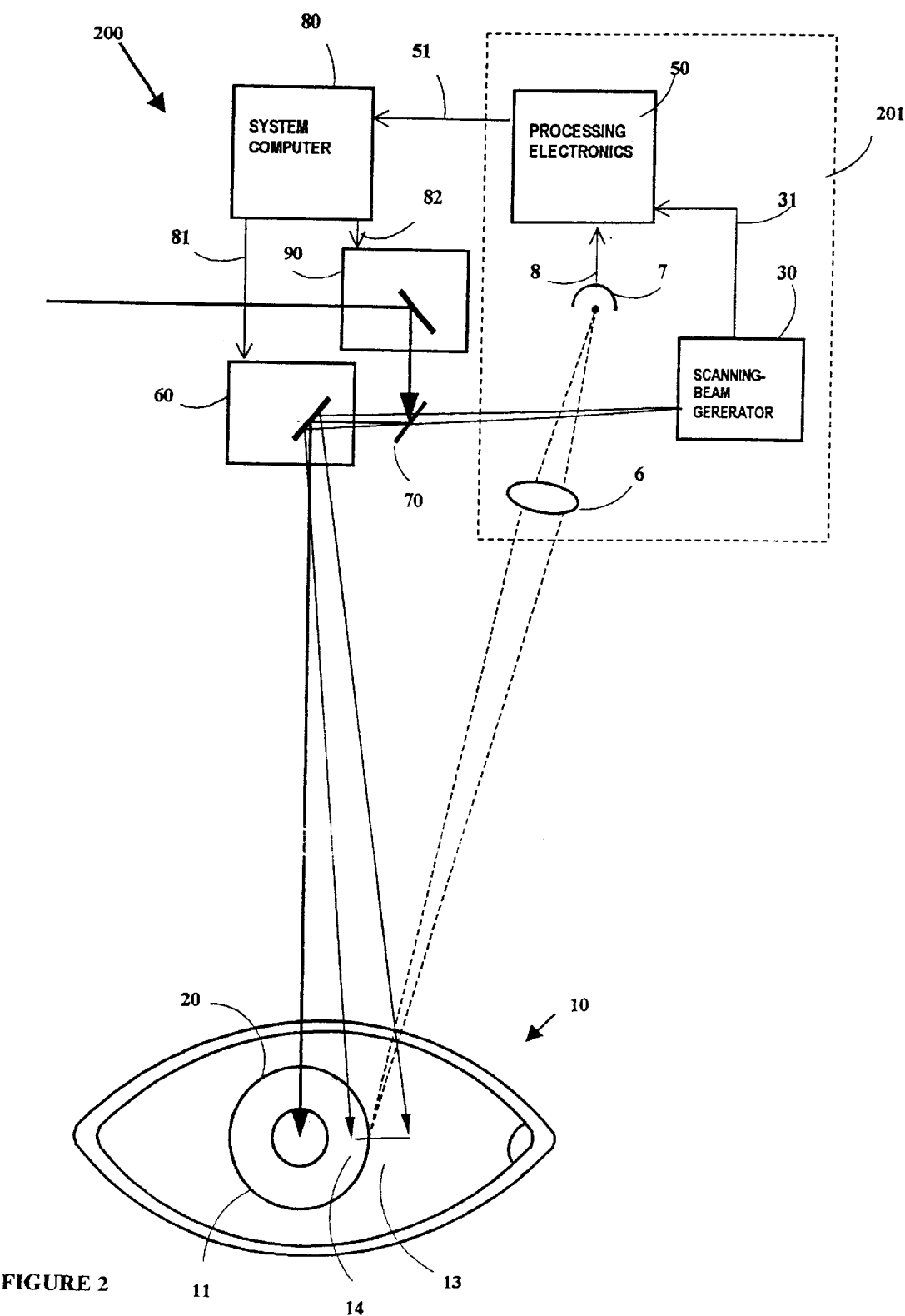
FIG. 2 is a schematic diagram showing an embodiment of a close-loop optical monitoring and tracking system.

FIG. 2 shows a schematic diagram of a close-loop tracking device 200. In the close-loop configuration, both the scanning beam 4 and the surgical beam 62 are steered to the eye 10 by a common steering module 60. Consequently, both the scanning probe beam 4 and the surgical laser beam 62 follow the movement of the eye 10.

In implementation, the scanning probe beam 4 is directed into the beam steering module 60 and reflected onto the reference mark 20 (i.e. the limbus 11). A dichromatic mirror 70 is placed in the path of the scanning probe beam 4 to couple the surgical laser beam 62 into the beam steering module 60. The dichromatic mirror 70 reflects light at the wavelength of the surgical laser beam 62 but transmits light at the wavelength of the scanning probe beam 4. The surgical laser beam 62 is reflected from the beam steering module 60 and projected onto the eye 10.

Again, the scattered light 5 from the reference mark 20 is collected by a lens 6 and detected by a photo-detector 7, which produces an output of scattered-light signal 8. Similar to the open loop device 100, the scatted-light signal 8 has a sharp step 9 corresponding to each scan of the probe beam 4 across the boundary of the reference mark 20. The sharp step 9 has a time delay Td with respect to the reference point 31s of corresponding scan. A processing electronics 50 determines this time delay Td for each scan.

To operate the tracking device 200, an initial time delay $Td_0$ or eye position is first registered and stored by the system computer 80. The time delay Td of later scans is then compared with the initial time delay $Td_0$. Any deviation of Td from $Td_0$ is used as an error signal to drive the beam steering module 60 such that to bring the error signal toward zero. Through this process, the beam steering module 60 deflects the scanning probe beam 4 to follow the movement of the eye 10. Seeing the same deflection as the scanning probe beam 4, the surgical laser beam 62 can thus impinge on any predetermined position of the eye 10 as if the eye remains stationary.

As a close loop device, the relative position between the trace of the scanning probe beam 4 and the reference mark 20 is kept constant during the operation. The beam steering module 60 is thus used solely for compensating the eye movement. A second beam steering module 90 is used to scan the surgical laser beam 62 on the eye 10 for surgery purpose. In this case, the control signal 81 to beam steering module 60 is simply the driving signal to compensate the eye movement. The control signal 82 to beam steering module 90 is simply the programmable signal to scan the surgical laser beam 62. The close loop device 200 is relatively more complicate but it can track a relative large displacement of the eye 10.

Figure 3A:
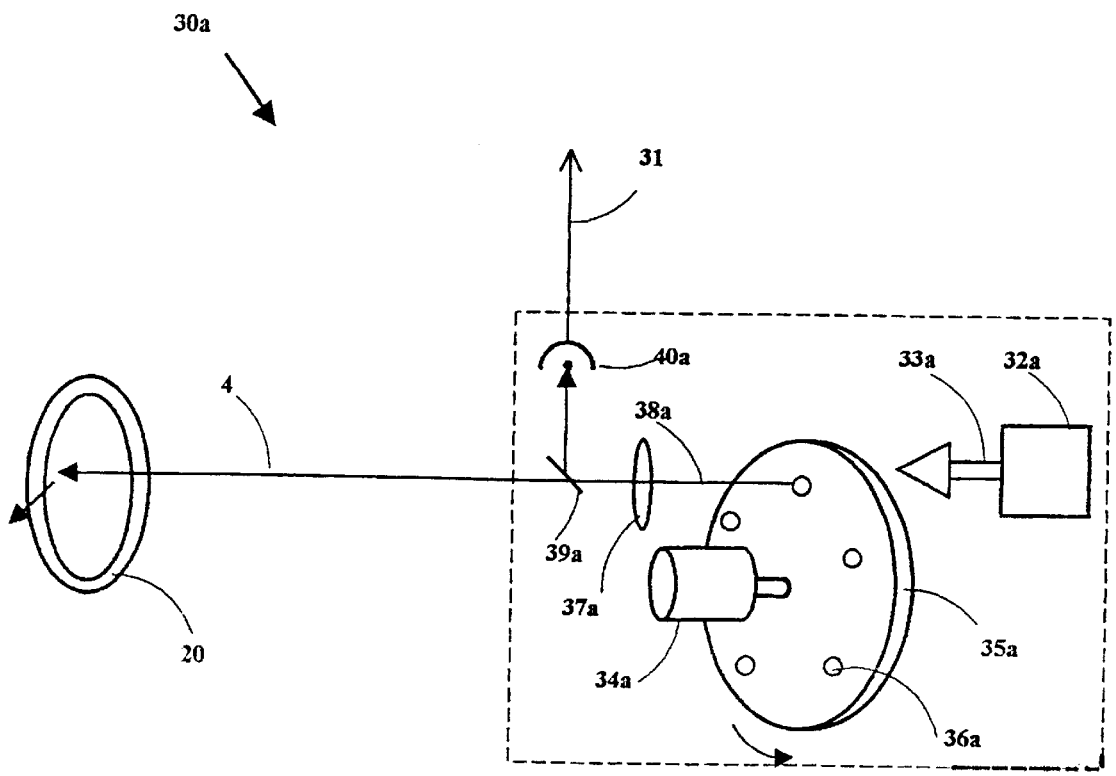
FIG. 3a is a schematic diagram showing one embodiment of a scanning-beam generator.

FIG. 3*a* shows one embodiment of a scanning-beam generator 30*a* that produces a scanning probe beam 4*a*. The generator 30*a* includes an infrared-light source 32*a*, which produces an infrared-light beam 33*a* projected onto a rotating blade 35*a*. The blade 35*a* has a set of pinholes 36*a* evenly distributed on a circle. A motor 34*a* drives the blade 35a at a constant rotation speed. The pinholes 36a are thus scanned across the infrared-light beam 33a at a constant speed.

A lens 37a focuses onto a reference ring 20 (i.e. the reference mark) the infrared-light beam 38a that is transmitted through the pinhole 36a. As the pinhole 36a is scanned across the infrared beam 33a, the image of the pinhole 36a is scanned across the reference ring 20. Thus, the transmitted infrared beam 38a may serve as the scanning probe beam 4 of FIG. 1.

A beam splitter 39a directs a small portion of the beam 38a onto a reference photo-detector 40a. This reference photo-detector 40a has a tiny light-sensitive area and the detected signal is thus a sequence of spikes as the split beam scans across the reference detector repetitively. The output signal from the photo-detector 40a defines a reference point of the scanning and serves as the reference signal 31 of FIG. 1.

In this embodiment, the infrared-light source 32a can be simply a light emitted diode. The repetition rate of the scanning probe beam 4 can be up to the kilohertz range. For example, the motor 34a may run at 100 rotation per second and the blade 35a may have 10 pinholes 36a on it.

Figure 3B:
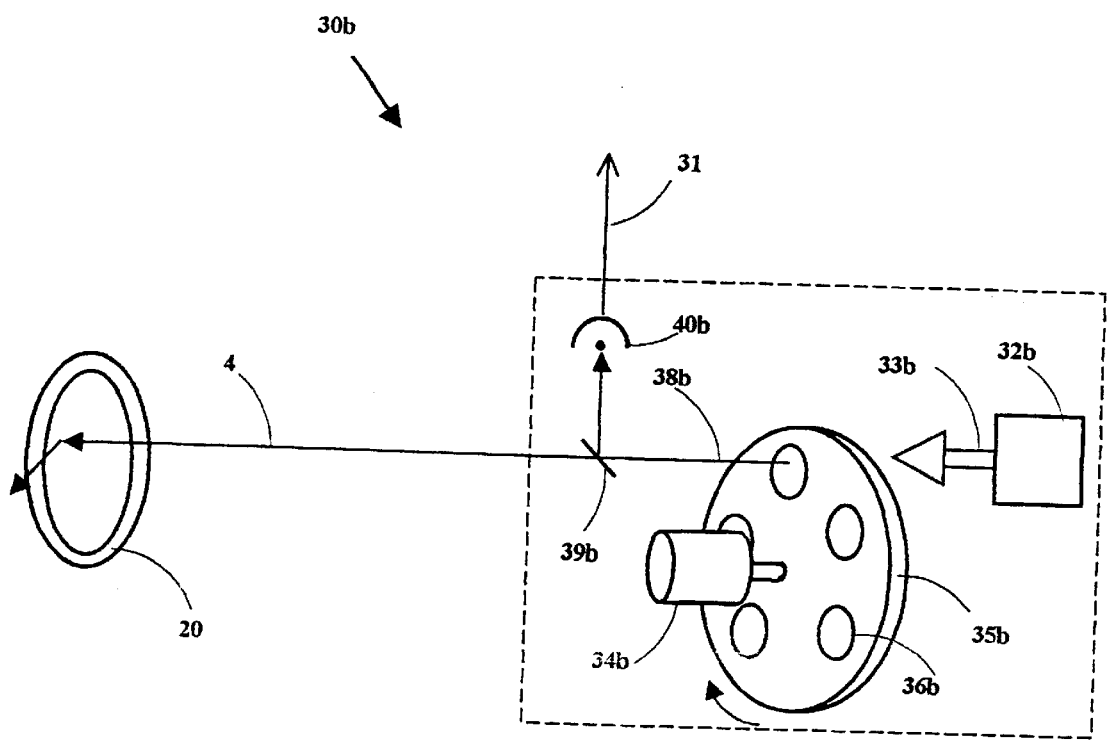
FIG. 3b is a schematic diagram showing another embodiment of a scanning-beam generator.

FIG. 3b shows another embodiment of a scanning-beam generator 30b producing a scanning probe beam 4. The generator 30b includes an infrared-light source 32b, which produces an infrared-light beam 33b directed onto a disk 35b. The disk 35b holds a set of identical lenses 36b evenly distributed on a circle. A motor 34b rotates the disk 35b and the lenses 36b are scanned across the infrared-light beam 33b at a constant speed.

The infrared-light beam 38b transmitted through a lens 36b is focused onto a reference ring 20. As the lens 36b is scanned across the infrared-light beam 33b, the focused beam 38b is scanned across the reference ring 20. Thus, the focused infrared-light beam 38b may serve as the scanning probe beam 4 of FIG. 1.

Again, a beam splitter 39b directs a small portion of the beam 38b onto a reference photo-detector 40b. The output signal from the photo-detector 40b defines a reference point of the scanning and serves as the reference signal 31 of FIG. 1. In this embodiment, the infrared-light source 32b is preferably either a pre-focused beam or a point source.

Figure 3C:
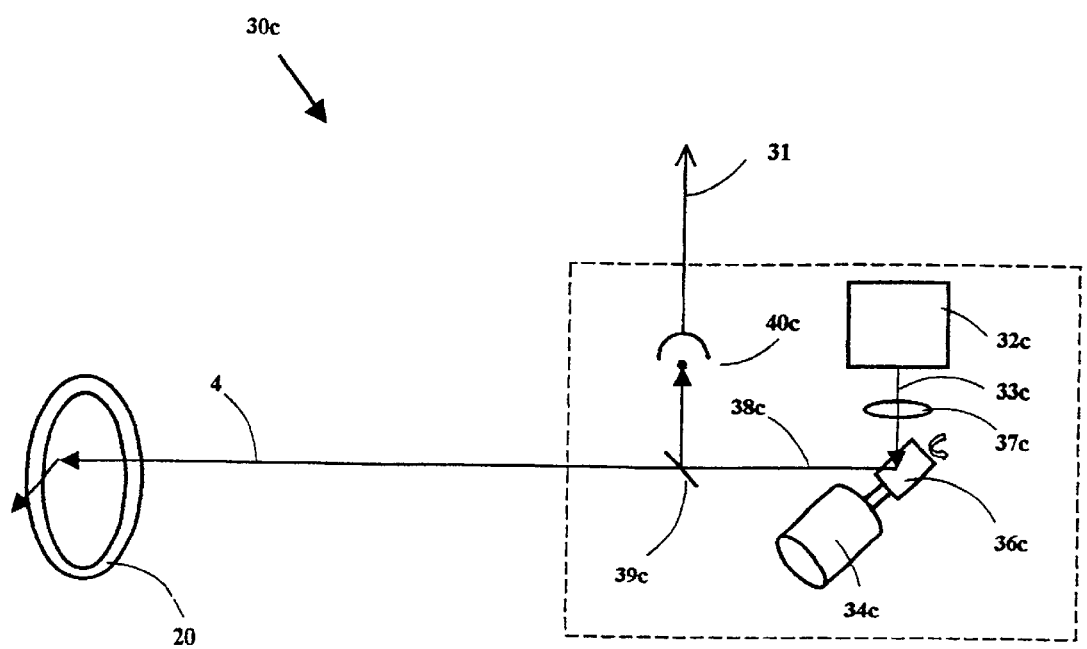
FIG. 3c is a schematic diagram showing a third embodiment of a scanning-beam generator.

FIG. 3c is a schematic diagram showing a third embodiment of a scanning-beam generator 30c producing a scanning probe beam 4. The generator 30c includes an infrared-light source 32c, which produces an infrared-light beam 33c directed into a lens 37c. The transmitted infrared beam 38c is reflected by a mirror 36c and focused onto a reference ring 20. The mirror 36c is driven by a scanner head 34c to scan the infrared beam 38c across the reference ring 20. Thus, the transmitted infrared beam 38a may serve as the scanning infrared beam 4 of FIG. 1.

Similarly, a beam splitter 39c directs a small portion of the beam 38c onto a reference photo-detector 40c. The output signal from the photo-detector 40c defines the reference point of the scanning and serves as the reference signal 31 of FIG. 1. The scanner 34c scans the beam 38c back and forth. A synchronized signal from the scanner 34c can also be used as a reference point of the scanning. In this embodiment, the infrared-light source 32c can be either a collimated beam or a point source.

Figure 4:
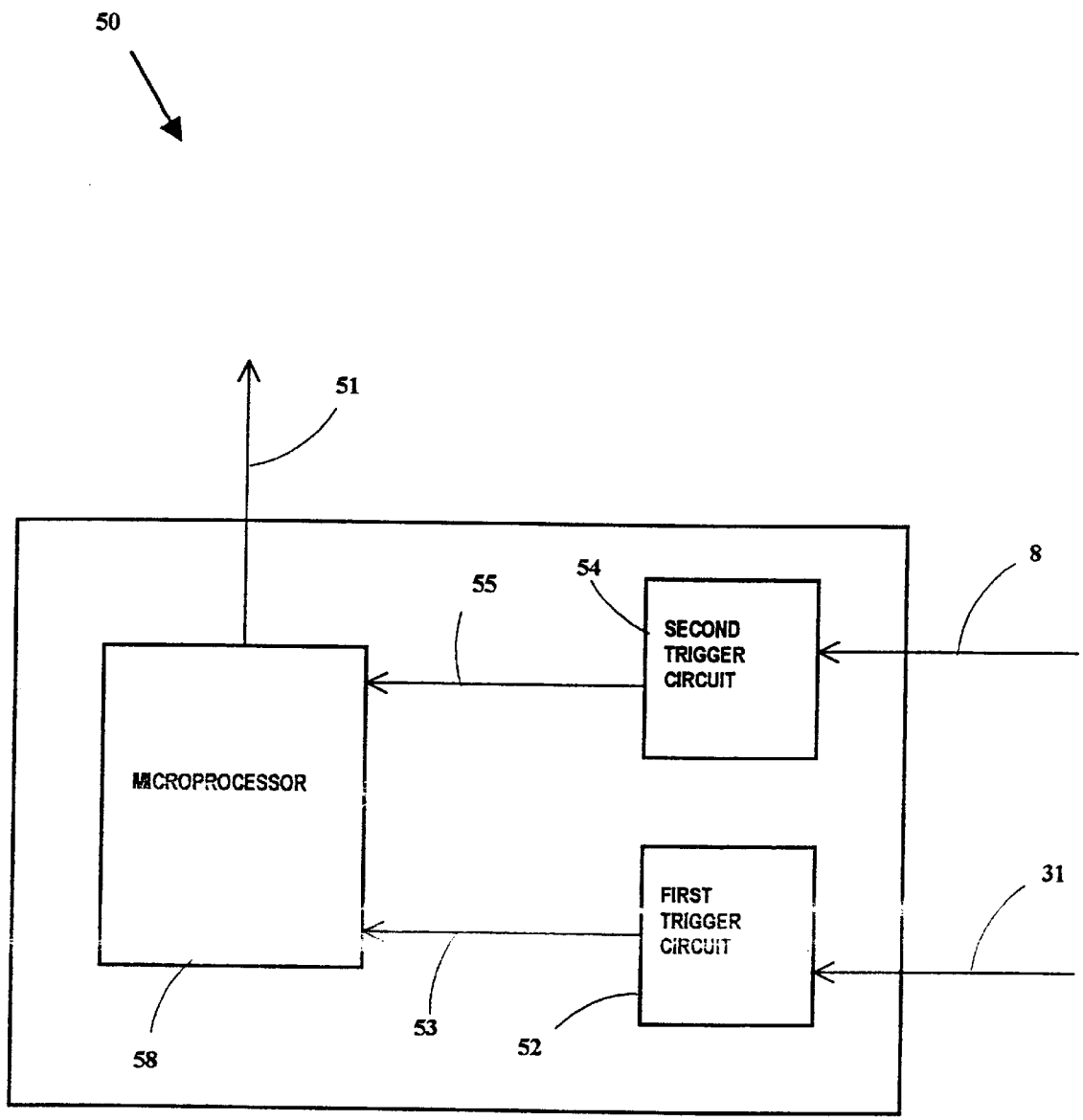
FIG. 4 is a block diagram showing a processing electronics for the optical monitoring and tracking systems of FIGS. 1 and 2.

FIG. 4 is a block diagram showing one embodiment of the processing electronics 50. This processing electronics 50 includes a first trigger circuit 52, a second trigger circuit 54, and a microprocessor 58. The reference signal 31 from the scanning beam generator 30 is fed into the first trigger circuit 52 to produce a TTL output signal 53 carrying the timing of the reference signal 31. The scattered-light signal 8 from the photo-detector 7 is fed into the second trigger circuit 54 to produce a TTL output signal 55 carrying the timing of the scattered-light signal 8.

The microprocessor 58 reads in the signal 53 and signal 55 to calculate a time delay Td between the two signals. This time delay Td indicates the relative position of the reference mark 20 to the scanning probe beam 4. This delay Td can be compared with an initial delay $Td_0$ registered and stored by the system computer 80 at the very beginning of the tracking.

For an open loop device 100, any change of the delay Td from its initial value $Td_0$ can be used to determine a displacement of the eye 10 from its initial position. The determined displacement can then be converted into an offset signal combined in the control signal 81 to deflect the surgical laser beam 62 to follow the movement of the eye 10.

For a close loop device 200, any deviation of the delay Td from its initial value $Td_0$ is used as an error signal to drive the beam steering module 60 such that to bring the error signal toward zero. The beam steering module 60 thus deflects both of the scanning probe beam 4 and the surgical laser beam 62 to follow the movement of the eye 10.

The above-described operation of the processing electronics 50 is repetitively for every scan of the probe beam 4. The first trigger circuit 52 and the second trigger circuit 54 should be reset automatically after the signal 53 and signal 55 are read by the microprocessor 58.

The processing electronics 50 shown in FIG. 4 is for one axis tracking. To track the two-dimensional movement of the eye 10, another pair of the trigger circuit should be used.

Figure 5A:
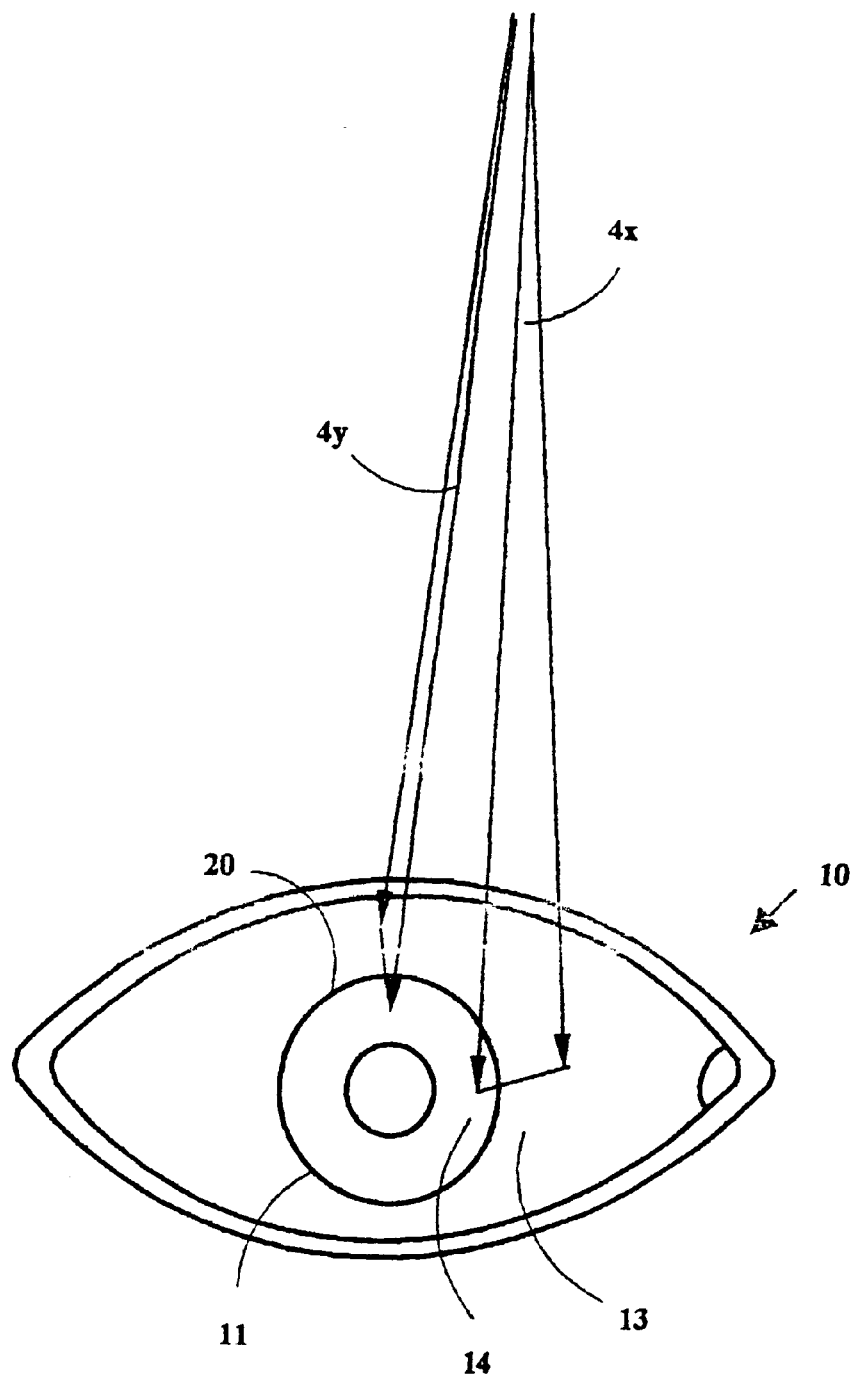
FIG. 5a is a schematic diagram illustrating simultaneous tracking of an eye in two different directions by two scanning probe beams projected on the limbus.

FIG. 5a shows schematically two scanning probe beams 4x and 4y projected on a reference ring 20 (the limbus 11) for two-dimension positioning detection. The two scanning probe beams 4x and 4y are set along two approximately perpendicular directions and occupy about one quart of the limbus 11.

Figure 5B:
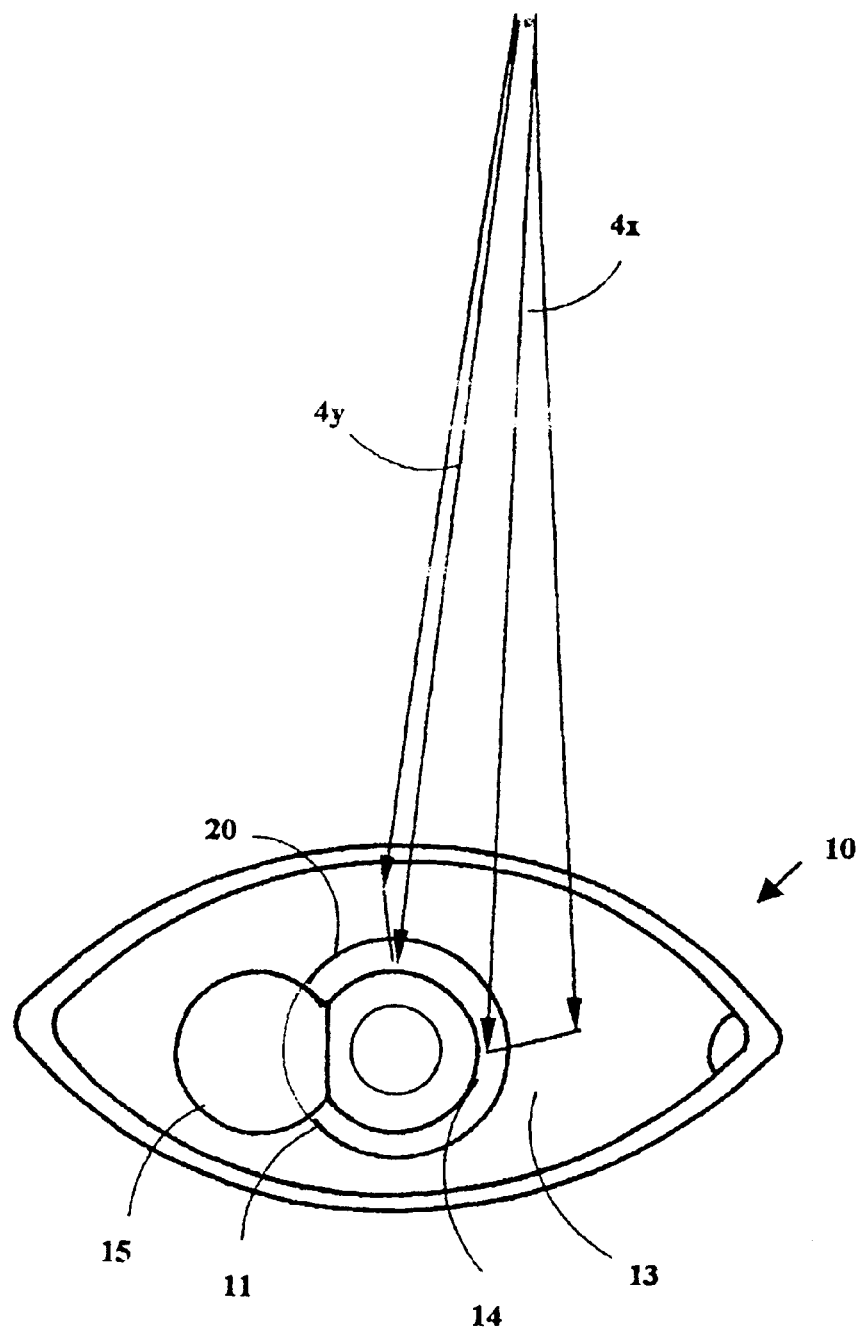
FIG. 5b shows two scanning probe beams projected on a partially obscured limbus to track the eye movement in two different directions in a LASIK surgery.

FIG. 5b shows how the tracking device remains fill performance for LASIK. In a LASIK surgery, a disk shape flap is laminated from the cornea and about one quart of the perimeter is uncut to maintain the flap attached to the cornea. The flap is folded over during the surgery to allow laser ablation on the corneal bed. The folded flap 15 covers about one third of the limbus 11 and may disable those eye tracking devices which rely on the whole limbus as the reference. The corneal bed after the flap is folded becomes less smooth and the scattered light from the corneal bed may disturb those tracking devices that use the pupil as a reference.

As illustrated in FIG. 5b, the two scanning beams 4x and 4y use only the limbus section that is not covered by the cornea flap 15. Therefore, the limbus 11 remains as a good reference for the tracking device of the present invention.

In all the above description, the tracking device is to steer a surgical laser beam 62 to follow the eye movement. Obviously, the same tracking mechanism can guide any other light beam or simply an optical path to follow the eye movement. Therefore, the above technique can be used to other surgical or diagnosis application in which compensating the eye movement is desirable.

Although the above embodiments are described with a specific reference to eye tracking, the techniques can be generally used to track lateral movement of other object with an optical reference mark. Various modifications can be made without departing from the scopes of the appended claims.

What is claimed is:

1. A method for optically tracking movement of an object, comprising:

selecting a reference mark on an object where first and second surface areas on opposite sides of the reference mark on the object are different in an optical property;

repetitively scanning an optical probe beam from the first surface area to the second surface area across the reference mark at a selected scanning speed along a selected direction so that a property of a scattered probe beam that is scattered from the object changes due to the change in the optical property in the first and second surface areas when the probe beam passes through the reference mark;

detecting a time at which the change in the property of the scattered probe beam occurs when the probe beam scans across the reference mark;

determining a time difference between the time and a reference time; and using the time difference to determine an amount of movement of the object along the selected direction.

2. The method as in claim 1, wherein the reference mark includes a boundary between the first and second surface areas with different optical reflectivities, and the property in the scattered probe beam is an optical amplitude.

3. The method as in claim 2, wherein the object is an eye and the reference mark includes the limbus of the eye with the sclera area being the first surface area and the cornea area being the second surface area.

4. The method as in claim 1, further comprising:

using the measured movement of the object along the selected direction to control a direction of another optical beam incident to the object to follow the movement of the object.

5. The method as in claim 4, further comprising:

scanning the other optical beam over the object according to a predetermined spatial pattern in addition to directing the other optical beam to track the object.

6. The method as in claim 1, further comprising:

selecting a second reference mark located between the first and second surface areas and orientated in a direction different from the reference mark;

repetitively scanning a second optical probe beam from the first surface area to the second surface area across the second reference mark at a second selected scanning speed along a second selected direction so that a property of a second scattered probe beam that is scattered from the object changes due to the change in the optical property in the first and second surface areas when the second probe beam passes through the second reference mark, wherein the second selected direction is different from the selected direction;

detecting a time at which the change in the property of the second scattered probe beam occurs when the second probe beam scans across the second reference mark;

determining a time difference between the time and a second reference time;

using the time difference to determine an amount of movement of the object along the second selected direction; and determining movement of the object in a surface defined by the selected direction and the second selected direction.

7. The method as in claim 6, wherein the second selected direction is substantially orthogonal to the selected direction.

8. The method as in claim 6, further comprising:

using the measured movement of the object along the selected direction and the second selected direction to control a direction of another optical beam incident to the object to follow the movement of the object.

9. The method as in claim 8, further comprising:

scanning the other optical beam over the object according to a predetermined spatial pattern in addition to directing the other optical beam to track the object.

10. The method as in claim 6, wherein the scanning of the probe beam is independent of the movement of the object.

11. The method as in claim 6, wherein the scanning of the probe beam is controlled to follow the movement of the object.

12. The method as in claim 1, wherein the scanning of the probe beam is independent of the movement of the object.

13. The method as in claim 1, wherein the scanning of the probe beam is controlled to follow the movement of the object.

14. An optical device, comprising:

a probe scanner to scan an optical probe beam across a reference mark on an object where first and second surface areas on opposite sides of the reference mark on the object are different in an optical property, said probe scanner operable to repetitively scan the optical probe beam from the first surface area to the second surface area across the reference mark at a selected scanning speed along a selected direction; and a probe detection unit positioned to receive a scattered probe beam that is scattered from the object and to detect a change in a property of the scattered probe beam due to the change in the optical property in the first and second surface areas when the probe beam passes through the reference mark, wherein said probe detection unit is operable to detect a time at which the change in the property of the scattered probe beam occurs and an amount of movement of the object along the selected direction according to a time difference between the time and a reference time.

15. The device as in claim 14, further comprising:

an optical scanner to receive and scan an optical beam over the object according to a selected spatial scanning pattern; and a control unit operable to control the optical scanner to track the movement of the object according to the detected amount of movement of the object, wherein scanning of said probe scanner is independent of the movement of the object.

16. The device as in claim 15, wherein the optical beam is operable to interact with the surface of the object so as to change a shape of the object and the probe beam does not change the shape of the object.

17. The device as in claim 14, further comprising:

an optical scanner to receive and scan an optical beam over the object according to a selected spatial scanning pattern;

a shared optical scanner positioned to receive both said optical beam from said optical scanner and said optical probe beam from said probe scanner and to direct both said optical beam and said probe beam to the object; and a control unit operable to control the shared optical scanner to control said optical beam and said probe beam to track the movement of the object according to the detected amount of movement of the object.

18. The device as in claim 14, wherein said probe scanner includes a probe light source to produce the probe beam, a projecting lens to project the probe beam, and a rotating wheel having a plurality of apertures located between the projecting lens and the probe light source.

19. The device as in claim 14, wherein said probe scanner includes a probe a probe light source to produce the probe beam, and a rotating wheel having a plurality of projecting lenses to rotate said projecting lenses into an optical path of the probe beam, one at a time.

20. The device as in claim 14, further comprising:

a second probe scanner to scan a second optical probe beam across a second reference mark located between the first and second surface areas and orientated in a direction different from the reference mark, said second probe scanner operable to repetitively scan the second probe beam at a second selected scanning speed across the second reference mark along a second selected direction, wherein a second scattered probe beam produced from scattering of the second probe beam from the object is detected to determine an amount of movement of the object along the second selected direction.

* * * * *